United States Patent
Mecklenburg

(10) Patent No.: US 11,584,945 B2
(45) Date of Patent: Feb. 21, 2023

(54) METHOD AND APPARATUS FOR IMPLEMENTING THRESHOLD BASED CORRECTION FUNCTIONS FOR BIOSENSORS

(71) Applicant: Ascensia Diabetes Care Holdings AG, Basel (CH)

(72) Inventor: George A. Mecklenburg, Elkhart, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 1101 days.

(21) Appl. No.: 16/222,555

(22) Filed: Dec. 17, 2018

(65) Prior Publication Data

US 2019/0119716 A1    Apr. 25, 2019

Related U.S. Application Data

(63) Continuation of application No. 10/592,218, filed as application No. PCT/US2005/011077 on Mar. 31, 2005, now abandoned.
(Continued)

(51) Int. Cl.
*C12Q 1/00* (2006.01)
*G01N 27/327* (2006.01)

(52) U.S. Cl.
CPC ......... *C12Q 1/006* (2013.01); *G01N 27/3274* (2013.01)

(58) Field of Classification Search
CPC ... C12Q 1/006; G01N 27/3274; G01N 27/416
See application file for complete search history.

(56) References Cited

U.S. PATENT DOCUMENTS 3,791,988 A   2/1974   Josef
4,746,607 A   5/1988   Mura
(Continued)

FOREIGN PATENT DOCUMENTS

CN   105378467 A  *  3/2016   ............ C12Q 1/006
EP   0 330 517 B1    4/1992
(Continued)

OTHER PUBLICATIONS

Skladl, P., "Compensation of Temperature Variations Disturbing Performance of an Amperometric Biosensor for Continuous Monitoring," Sensors and Actuators B, Elsevier Sequoia S.A., Lausanne, CH, vol. 28, No. 1, Jul. 1995 (4 pages).
(Continued)

*Primary Examiner* — Francis C Gray
(74) *Attorney, Agent, or Firm* — Erise IP, P.A.

(57) ABSTRACT

A biosensor system, method and apparatus are provided for implementing threshold based correction functions for biosensors. A primary measurement of an analyte value is obtained. A secondary measurement of a secondary effect is obtained and is compared with a threshold value. A correction function is identified responsive to the compared values. The correction function is applied to the primary measurement of the analyte value to provide a corrected analyte value. The correction method uses correction curves that are provided to correct for an interference effect. The correction curves can be linear or non-linear. The correction method provides different correction functions above and below the threshold value. The correction functions may be dependent or independent of the primary measurement that is being corrected. The correction functions may be either linear or nonlinear.

17 Claims, 4 Drawing Sheets

Related U.S. Application Data

(60) Provisional application No. 60/609,570, filed on Sep. 13, 2004, provisional application No. 60/557,907, filed on Mar. 31, 2004.

(56) References Cited

U.S. PATENT DOCUMENTS

| | | | |
|---|---|---|---|
| 4,929,545 | A | 5/1990 | Freitag |
| 6,391,645 | B1 | 5/2002 | Huang |
| 6,645,368 | B1 | 11/2003 | Beaty |
| 7,018,843 | B2 | 3/2006 | Heller |
| 7,167,776 | B2 | 1/2007 | Maharajh |
| 7,338,639 | B2 | 3/2008 | Burke |
| 9,243,276 | B2 * | 1/2016 | Malecha ............ G01N 27/3274 |
| 9,904,761 | B2 * | 2/2018 | Vandersleen ...... G01N 27/3273 |
| 2001/0016682 | A1 * | 8/2001 | Berner ................ A61B 5/14542 600/347 |
| 2002/0125145 | A1 | 9/2002 | Ohara |
| 2007/0111197 | A1 * | 5/2007 | Hirayama .............. G16H 10/20 702/19 |
| 2009/0236237 | A1 * | 9/2009 | Shinno ............. G01N 33/54393 205/792 |
| 2010/0206749 | A1 * | 8/2010 | Choi .................. G01N 27/3274 204/403.01 |
| 2011/0272294 | A1 * | 11/2011 | Fujiwara ............ G01N 27/3272 205/792 |
| 2013/0306493 | A1 * | 11/2013 | Chatelier ................ C12Q 1/006 205/782 |
| 2015/0068922 | A1 * | 3/2015 | Mackintosh ........... C12Q 1/006 204/403.02 |
| 2019/0119716 | A1 * | 4/2019 | Mecklenburg .......... C12Q 1/006 |
| 2019/0177764 | A1 * | 6/2019 | Wieder ............... G01N 27/3274 |

FOREIGN PATENT DOCUMENTS

| | | |
|---|---|---|
| EP | 0 354 441 B1 | 5/1995 |
| EP | 1 394 545 A1 | 3/2004 |
| EP | 0 878 713 A3 | 6/2004 |
| JP | H04-328459 | 11/1992 |
| JP | H10-318963 | 12/1998 |
| JP | 2001-527215 | 12/2001 |
| JP | 2003-156469 | 5/2003 |
| JP | 2003-521708 | 7/2003 |
| JP | 2004-163411 | 6/2004 |
| WO | WO 99/32881 | 7/1999 |

OTHER PUBLICATIONS

International Search Report in International Patent Application No. PCT/US2005/011077, dated Aug. 8, 2005 (6 pages).

Written Opinion in International Patent Application No. PCT/US2005/011077, dated Aug. 8, 2005 (4 pages).

* cited by examiner

METHOD AND APPARATUS FOR IMPLEMENTING THRESHOLD BASED CORRECTION FUNCTIONS FOR BIOSENSORS

CROSS-REFERENCE TO RELATED APPLICATIONS

This application is a continuation of application Ser. No. 10/592,218 filed Sep. 8, 2006; application Ser. No. 10/592,218 is a U.S. National Phase Filing of International Application No. PCT/US2005/011077, filed on Mar. 31, 2005; International Application No. PCT/US2005/011077, filed on Mar. 31, 2005 claims the benefit of Application Nos. 60/557,907, filed Mar. 31, 2004 and 60/609,570, filed Sep. 13, 2004. All of these applications are incorporated by reference in their entireties.

FIELD OF THE INVENTION

The present invention relates generally to biosensors, and more particularly, relates to a method and apparatus for implementing threshold based correction functions for biosensors.

DESCRIPTION OF THE RELATED ART

The quantitative determination of analytes in body fluids is of great importance in the diagnoses and maintenance of certain physiological abnormalities. For example lactate, cholesterol and bilirubin should be monitored in certain individuals. In particular, the determination of glucose in body fluids is of great importance to diabetic individuals who must frequently check the level of glucose in their body fluids as a means of regulating the glucose intake in their diets. While the remainder of the disclosure herein will be directed towards the determination of glucose, it is to be understood that the procedure and apparatus of this invention can be used for the determination of other analytes upon selection of the appropriate enzyme. The ideal diagnostic device for the detection of glucose in fluids must be simple, so as not to require a high degree of technical skill on the part of the technician administering the test. In many cases, these tests are administered by the patient which lends further emphasis to the need for a test which is easy to carry out. Additionally, such a device should be based upon elements which are sufficiently stable to meet situations of prolonged storage.

Methods for determining analyte concentration in fluids can be based on the electrochemical reaction between an enzyme and the analyte specific to the enzyme and a mediator which maintains the enzyme in its initial oxidation state. Suitable redox enzymes include oxidases, dehydrogenases, catalase and peroxidase. For example, in the case where glucose is the analyte, the reaction with glucose oxidase and oxygen is represented by equation (A).

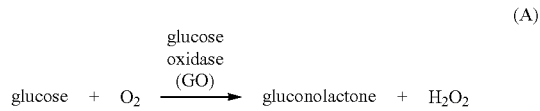
(A)

In a colorimetric assay, the released hydrogen peroxide, in the presence of a peroxidase, causes a color change in a redox indicator which color change is proportional to the level of glucose in the test fluid. While colorimetric tests can be made semi-quantitative by the use of color charts for comparison of the color change of the redox indicator with the color change obtained using test fluids of known glucose concentration, and can be rendered more highly quantitative by reading the result with a spectrophotometric instrument, the results are generally not as accurate nor are they obtained as quickly as those obtained using an electrochemical biosensor. As used herein, the term biosensor system refer to an analytical device that responds selectively to analytes in an appropriate sample and converts their concentration into an electrical signal via a combination of a biological recognition signal and a physico-chemical transducer.

$$H_2O_2 \rightarrow O_2 + 2H^+ + 2e^- \qquad (B)$$

The electron flow is then converted to the electrical signal which directly correlates to the glucose concentration.

In the initial step of the reaction represented by equation (A), glucose present in the test sample converts the oxidized flavin adenine dinucleotide (FAD) center of the enzyme into its reduced form, ($FADH_2$). Because these redox centers are essentially electrically insulated within the enzyme molecule, direct electron transfer to the surface of a conventional electrode does not occur to any measurable degree in the absence of an unacceptably high overvoltage. An improvement to this system involves the use of a nonphysiological redox coupling between the electrode and the enzyme to shuttle electrons between the ($FADH_2$) and the electrode. This is represented by the following scheme in which the redox coupler, typically referred to as a mediator, is represented by M:

$$Glucose + GO(FAD) \rightarrow gluconolactone + GO(FADH_2)$$

$$GO(FADH_2) + 2M_{OX} \rightarrow GO(FAD) + 2M_{red} + 2H^+$$

$$2M_{red} \rightarrow 2M_{OX} + 2e^- \text{ (at the electrode)}$$

In this scheme, GO(FAD) represents the oxidized form of glucose oxidase and GO($FADH_2$) indicates its reduced form. The mediating species $M_{red}$ shuttles electrons from the reduced enzyme to the electrode thereby oxidizing the enzyme causing its regeneration in situ which, of course, is desirable for reasons of economy. The main purpose for using a mediator is to reduce the working potential of the sensor. An ideal mediator would be re-oxidized at the electrode at a low potential under which impurity in the chemical layer and interfering substances in the sample would not be oxidized thereby minimizing interference.

Many compounds are useful as mediators due to their ability to accept electrons from the reduced enzyme and transfer them to the electrode. Among the mediators known to be useful as electron transfer agents in analytical determinations are the substituted benzo- and naphthoquinones disclosed in U.S. Pat. No. 4,746,607; the N-oxides, nitroso compounds, hydroxylamines and oxines specifically disclosed in EP 0 354 441; the flavins, phenazines, phenothiazines, indophenols, substituted 1,4-benzoquinones and indamins disclosed in EP 0 330 517 and the phenazinium/phenoxazinium salts described in U.S. Pat. No. 3,791,988. A comprehensive review of electrochemical mediators of biological redox systems can be found in *Analytica Clinica Acta.* 140 (1982), Pp 1-18.

Among the more venerable mediators is hexacyanoferrate, also known as ferricyanide, which is discussed by Schläpfer et al in *Clinica Chimica Acta.*, 57 (1974), Pp. 283-289. In U.S. Pat. No. 4,929,545 there is disclosed the use of a soluble ferricyanide compound in combination with a soluble ferric compound in a composition for enzymatically determining an analyte in a sample. Substituting the iron salt of ferricyanide for oxygen in equation (A) provides:

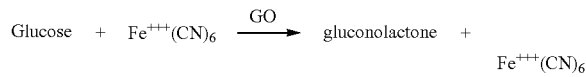

since the ferricyanide is reduced to ferrocyanide by its acceptance of electrons from the glucose oxidase enzyme.

Another way of expressing this reaction is by use of the following equation (C):

$$Glucose + GO_{X(OX)} \rightarrow Gluconalactone + GO_{X(red)}$$

$$GO_{X(red)} + 2Fe(CN_3)^{3-}{}_6 \rightarrow GO_{X(OX)} + 2Fe(CN)^{4-} + 2e^- \quad (C)$$

The electrons released are directly equivalent to the amount of glucose in the test fluid and can be related thereto by measurement of the current which is produced through the fluid upon the application of a potential thereto. Oxidation of the ferrocyanide at the anode renews the cycle.

U.S. Pat. No. 6,391,645 to Huang et al., issued May 21, 2002 and assigned to the present assignee, discloses a method and apparatus for correcting ambient temperature effect in biosensors. An ambient temperature value is measured. A sample is applied to the biosensors, then a current generated in the test sample is measured. An observed analyte concentration value is calculated from the current through a standard response curve. The observed analyte concentration is then modified utilizing the measured ambient temperature value to thereby increase the accuracy of the analyte determination. The analyte concentration value can be calculated by solving the following equation:

$$G2=(G1-(T_2{}^2-24^2)*I2-(T_2-24)*I1)/((T_2{}^2-24^2)*S2+(T_2-24)*S1+1)$$

where G1 is said observed analyte concentration value, $T_2$ is said measured ambient temperature value and I1, I2, S1, and S2 are predetermined parameters.

While the method and apparatus disclosed by U.S. Pat. No. 6,391,645 provided improvements in the accuracy of the analyte determination, a need exists for an improved correction mechanism and that can be applied to any system that measures an analyte concentration.

As used in the following specification and claims, the term biosensor means an electrochemical sensor strip or sensor element of an analytical device or biosensor system that responds selectively to an analyte in an appropriate sample and converts their concentration into an electrical signal. The biosensor generates an electrical signal directly, facilitating a simple instrument design. Also, a biosensor offers the advantage of low material cost since a thin layer of chemicals is deposited on the electrodes and little material is wasted.

The term sample is defined as a composition containing an unknown amount of the analyte of interest. Typically, a sample for electrochemical analysis is in liquid form, and preferably the sample is an aqueous mixture. A sample may be a biological sample, such as blood, urine or saliva. A sample may be a derivative of a biological sample, such as an extract, a dilution, a filtrate, or a reconstituted precipitate.

The term analyte is defined as a substance in a sample, the presence or amount of which is to be determined. An analyte interacts with the oxidoreductase enzyme present during the analysis, and can be a substrate for the oxidoreductase, a coenzyme, or another substance that affects the interaction between the oxidoreductase and its substrate.

SUMMARY OF THE INVENTION

Important aspects of the present invention are to provide a new and improved biosensor system for determining the presence or amount of a substance in a sample including a method and apparatus for implementing threshold based correction functions for biosensors.

In brief, a method and apparatus are provided for implementing threshold based correction functions for biosensors. A sample is applied to the biosensor and a primary measurement of an analyte value is obtained. A secondary measurement of a secondary effect is obtained and is compared with a threshold value. A correction function is identified responsive to the compared values. The correction function is applied to the primary measurement of the analyte value to provide a corrected analyte value.

In accordance with features of the invention, the correction method uses correction curves that are provided to correct for an interference effect. The correction curves can be linear or non-linear. The correction method provides different correction functions above and below the threshold value. The correction functions may be dependent or independent of the primary measurement that is being corrected. The correction functions may be either linear or nonlinear.

In accordance with features of the invention, the secondary measurement of a secondary effect includes a plurality of effects that are use separately or together in combination to identify the correction function. For example, the secondary effects include temperature, Hemoglobin, and the concentration of hematocrit of a blood sample that are identified and used to minimize the interference of the secondary effects on the accuracy of the reported results.

BRIEF DESCRIPTION OF THE DRAWING

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
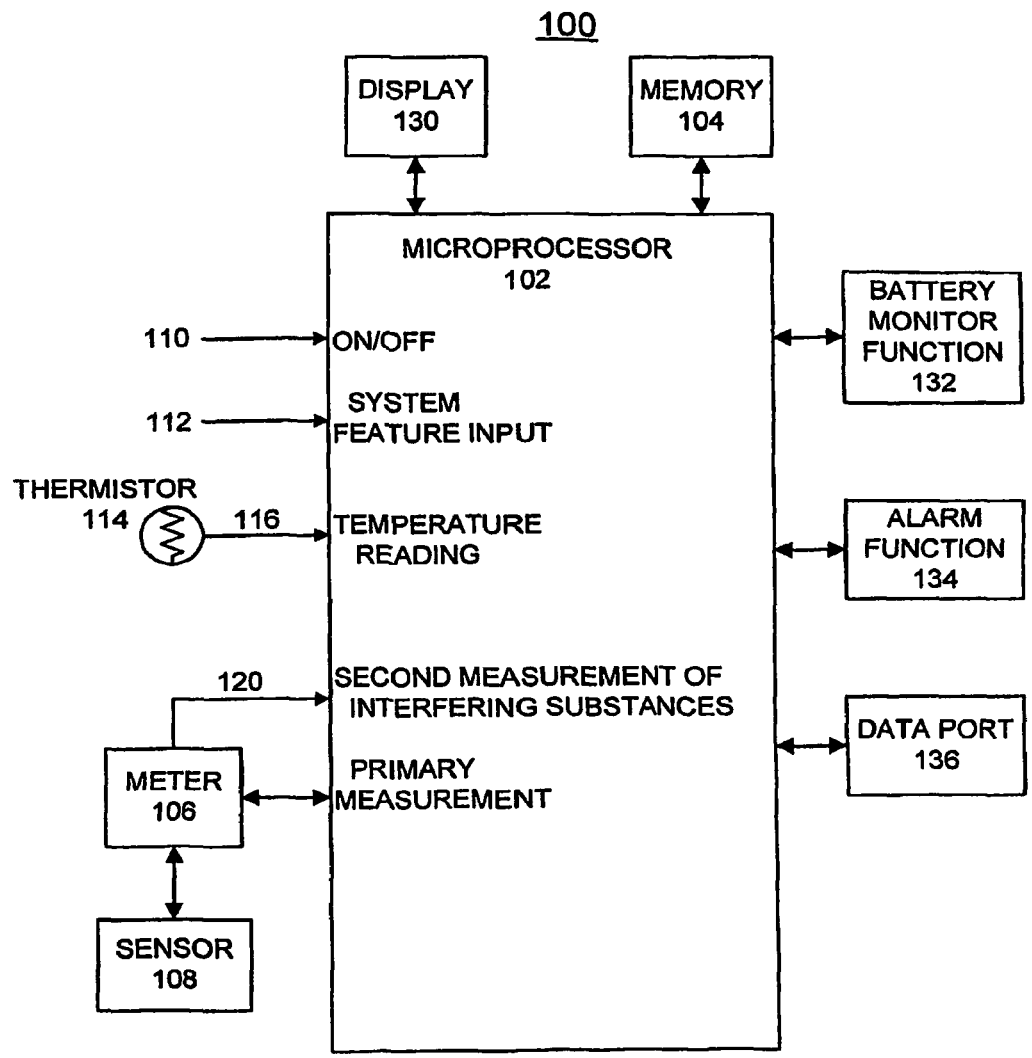
FIG. 1 is a block diagram representation of biosensor system in accordance with the present invention.

Having reference now to the drawings, in FIG. 1 there is shown a block diagram representation of biosensor system designated as a whole by the reference character 100 and arranged in accordance with principles of the present invention. Biosensor system 100 includes a microprocessor 102 together with an associated memory 104 for storing program and user data and correction curves for implementing threshold based correction of secondary effects in accordance with the present invention. A meter function 106 coupled to a biosensor 108 is operatively controlled by the microprocessor 102 for recording test values, such as blood glucose test values. An ON/OFF input at a line 110 responsive to the user ON/OFF input operation is coupled to the microprocessor 102 for performing the blood test sequence mode of biosensor system 100. A system features input at a line 112 responsive to a user input operation is coupled to the microprocessor 102 for selectively performing the system features mode of biosensor 100. A thermistor 114 provides a temperature signal input indicated at a line 116 is coupled to the microprocessor 102 for detecting interfering effects, for example, the temperature information for the sensor 108 in accordance with the invention. A signal input indicated at a line 120 is coupled to the microprocessor 102 for a second measure of interfering substances, for example, Hemoglobin, optionally provided by the meter function 106.

Figure 2:
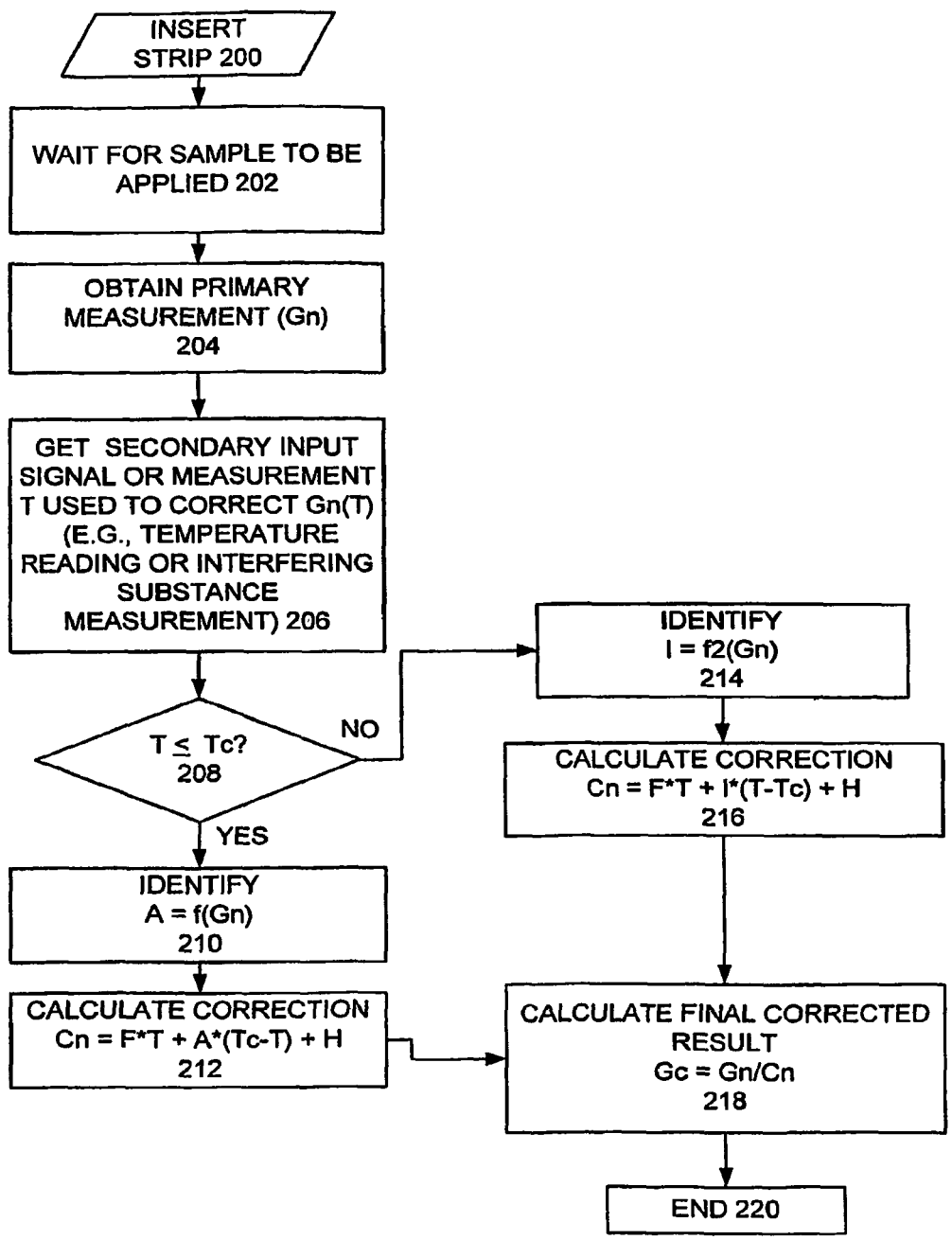
FIG. 2 is a flow chart illustrating exemplary logical steps performed in accordance with the present invention of the method for implementing threshold based correction of secondary effects, such as correcting ambient temperature effect, in the biosensor system of FIG. 1.

A display 130 is coupled to the microprocessor 102 for displaying information to the user including test results. A battery monitor function 132 is coupled to the microprocessor 102 for detecting a low or dead battery condition. An alarm function 134 is coupled to the microprocessor 102 for detecting predefined system conditions and for generating alarm indications for the user of biosensor system 100. A data port or communications interface 136 is provided for coupling data to and from a connected computer (not shown). Microprocessor 102 contains suitable programming to perform the methods of the invention as illustrated in FIG. 2.

Biosensor system 100 is shown in simplified form sufficient for understanding the present invention. The illustrated biosensor system 100 is not intended to imply architectural or functional limitations. The present invention can be used with various hardware implementations and systems.

In accordance with the invention, biosensor system 100 performs a correction method of the preferred embodiment, for example, to reduce the temperature bias having a general form as shown in the following TABLE 1 and as illustrated and described with respect to FIG. 2. This invention provides an algorithmic correction method that advantageously improves the accuracy of diagnostic chemistry tests by correcting for secondary effects, such as interfering substances or temperature effects.

It should be understood that the present invention can be applied to any system, electrochemical or optical, that measures an analyte concentration as a primary measurement and then uses a second measure of interfering substances, for example, Hemoglobin, or interfering effects for example, temperature, to compensate for the secondary effect and improve the accuracy of the reported result.

It is also desirable to minimize the interference from hematocrit or volume fraction of erythrocytes on the accuracy of the reported results. The conductivity or impedance of whole blood is dependent on the concentration of hematocrit. Meter function 106 can be used to measure the resistance of the sample fluid at signal input line 120 and the measured value advantageously used to correct for the effect of hematocrit on the reported result. For example, the measured resistance advantageously is used to estimate the concentration of hematocrit of a blood sample and then to correct the measurement for hematocrit effect for determining the concentration of a substance of interest in blood. This invention provides an algorithmic correction method that advantageously improves the accuracy of diagnostic chemistry tests by correcting for secondary effects including interference from hematocrit and temperature effects.

Figure 3:
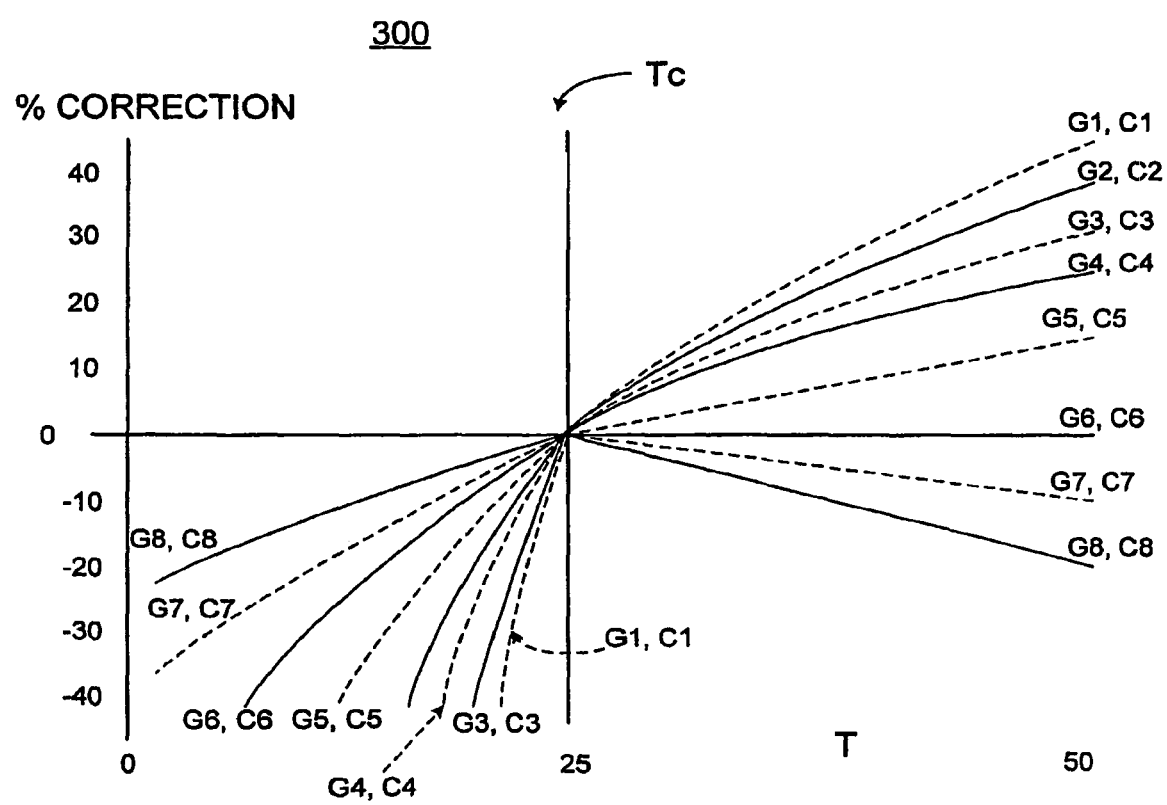
FIGS. 3 and 4 are graphs of exemplary stored correction curves illustrating corrections characteristics in accordance with the present invention.
Figure 4:
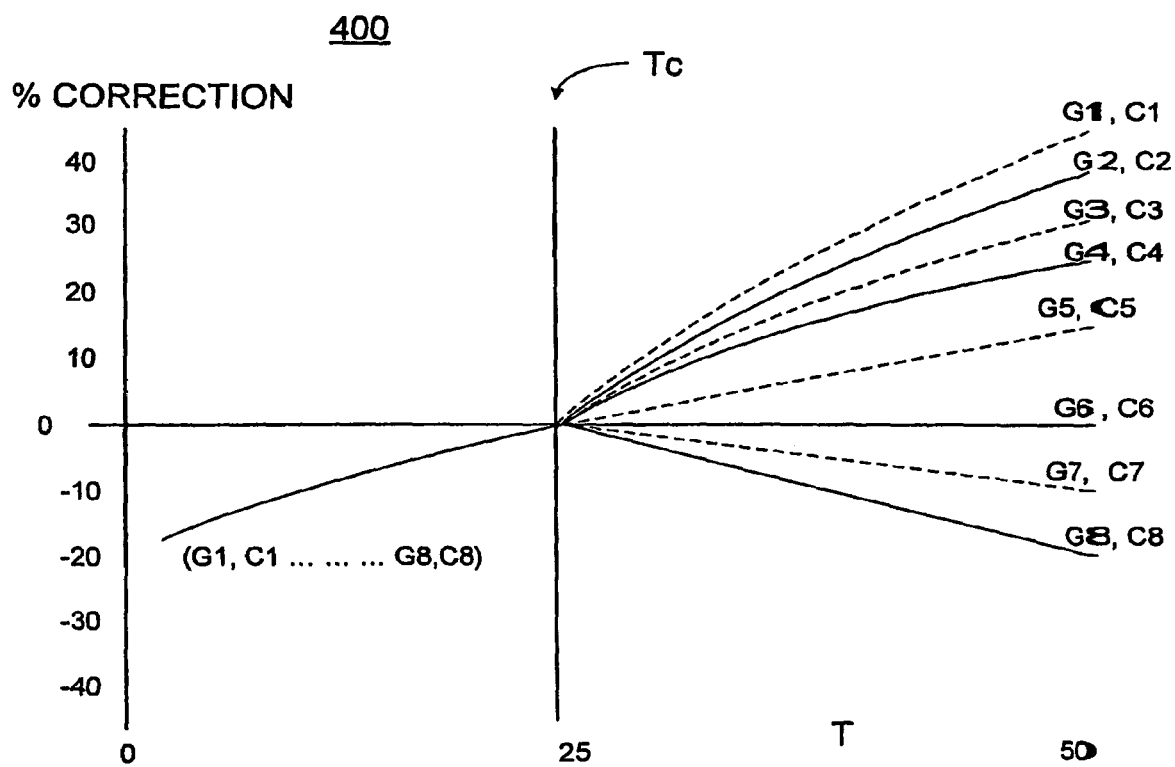

In accordance with the invention, the algorithmic correction method uses correction curves, for example, as illustrated and described with respect to FIGS. 3 and 4, that can be tailored to correct for any well-defined interference effect. The correction curves can be linear or non-linear. The algorithmic correction method has characteristics that can be modified by changing only the equation coefficients as follows. First, different correction functions can be provided above and below a threshold. Second, the correction functions may be dependent or independent of the primary measurement that is being corrected. Third, functions used for correction may be either linear or nonlinear.

TABLE 1

General Correction Algorithm Form

Step 1. Obtain primary measurement ($G_n$).
Step 2. Obtain secondary measurement used to correct $G_n(T)$
Step 3A If $T \le T_c$ then:
1. $A = f(G_n)$
2. $C_n = F * T + A * (T_c - T) + H$
Step 3B If $T > T_c$ then:
3. $I = f_2(G_N)$
4. $C_n = F*T + I*(T - Tc) + H$
5. $G_c = (G_n / C_n)$ Where:
$G_n$ = Uncorrected measurement of analyte concentration;
$T$ = Secondary measurement used to correct primary measurement;
$T_c$ = Decision point or threshold, secondary measurements greater of less than threshold advantageously can use different correction functions;
$G_c$ = Final corrected result; and
A, I, F, H, are coefficients that control magnitude of correction lines or define correction curves.

Referring now to FIG. 2, there are shown exemplary logical steps performed in accordance with the present invention of the method for implementing threshold based correction of secondary effects, such as correcting ambient temperature effect, in the biosensor system 100. A strip is inserted as indicated in a block 200 and then waiting for a sample to be applied is performed as indicated in a block 202. A primary measurement Gn is obtained as indicated in a block 204. Then a secondary measurement T to be used for correction Gn(T) is obtained as indicated in a block 206. The secondary measurement T is compared with the threshold value Tc as indicated in a decision block 208. If the secondary measurement T is less than or equal to the threshold value Tc, then a coefficient A to control magnitude of the correction is identified as indicated in a block 210, where A=f(Gn). Then a correction Cn is calculated as indicated in a block 210, where $C_n = F*T+A*(T_c-T)+H$. Otherwise If the secondary measurement T is greater than the threshold value Tc, then a coefficient I to control magnitude of the correction is identified as indicated in a block 214, where I=f2(Gn). Then a correction Cn is calculated as indicated in a block 216, where $C_n = F*T+I*(T-T_c)+H$. A final corrected result Gc is calculated as indicated in a block 218, where Gc=Gn/Cn to complete the correction algorithm as indicated in a block 220.

Referring now to FIGS. 3 and 4, there are shown respective first and second examples generally designated by reference characters 300 and 400 illustrating exemplary theoretical lines of correction. In FIGS. 3 and 4, a percentage (%) correction is illustrated relative to a vertical axis and a secondary measurement T is illustrated relative to a horizontal axis. A threshold value Tc is indicated by a line labeled Tc.

FIG. 3 illustrates isometric correction lines at different primary measurement concentrations Gn where the correction is dependent on the primary measurement concentrations Gn. As shown in the example 300 in FIG. 3, the magnitude of the correction Cn changes with analyte concentration Gn when the secondary measurement T is above or below the threshold Tc. FIG. 4 illustrates isometric correction lines at different primary measurement concentrations Gn where the correction is dependent on the primary measurement concentrations Gn above the threshold value Tc and is constant and independent of the primary measurement concentrations Gn below and equal to the threshold value Tc.

While the present invention has been described with reference to the details of the embodiments of the invention shown in the drawing, these details are not intended to limit the scope of the invention as claimed in the appended claims.

What is claimed is:

1. A method for measuring a glucose analyte value in a blood sample via a biosensor, the method comprising:
    applying a fluid sample to a sensor element on a sensor strip of an electrochemical biosensor and obtaining an electrical output signal representing a primary measurement of the glucose analyte value, the biosensor being coupled to a meter function;
    obtaining a secondary measurement of a secondary effect via a secondary sensor or the meter function;
    comparing said secondary measurement of the secondary effect with a threshold value stored in a memory via at least one processor with a meter input coupled to the meter function;
    selecting, by the at least one processor, a first correction function from a plurality of correction functions if the secondary measurement is less than the threshold value;
    selecting, by the at least one processor, a second correction function from the plurality of correction functions if the secondary measurement is greater than the threshold value,
    wherein the first correction function and the second correction function comprise stored data indicative of a correction amount as a function of the secondary measurement;
    wherein the first correction function and the second correction function differ only by coefficient values;
    applying the primary measurement to the first correction function or the second correction function via the at least one processor to provide a corrected analyte value; and
    causing for display the corrected analyte value on a display communicatively coupled to the at least one processor.

2. The method of claim 1 wherein a first coefficient A is a function of the primary measurement, and the first coefficient A controls a magnitude of the first correction function.

3. The method of claim 2,
    wherein a correction value of the first correction function is represented by $$C_n = F*T + A*(T_c - T) + H,$$

where T represents said secondary measurement of the secondary effect, Tc represents the threshold value; and F and H are predefined coefficients.

4. The method of claim 3, wherein the applying the the primary measurement to the first correction function to provide the corrected analyte value further includes calculating the corrected analyte value represented by Ge=Gn/Cn, where Gn represents the primary measurement of the glucose analyte value.

5. The method of claim 1, wherein the second correction function includes identifying a second coefficient I, wherein the second coefficient I is a function of the primary measurement, and the second coefficient I is used to control magnitude of the second correction function.

6. The method of claim 2, wherein the correction value of the second correction function is represented by $$C_n = F*T + A*(T_c - T) + H,$$

where T represents said secondary measurement of the secondary effect, Tc represents the threshold value; and F and H are predefined coefficients.

7. The method of claim 6, wherein the applying the primary measurement to the second correction function to provide a corrected analyte value further includes calculating the corrected analyte value represented by Ge=Gn/Cn, where Gn represents the primary measurement of the glucose analyte value.

8. The method of claim 1, wherein a plurality of predefined correction curves is stored in the memory and wherein the plurality of predefined correction curves is provided to correct for an interference effect.

9. The method of claim 1, wherein the first correction function or the second correction function is a linear function.

10. The method of claim 1, wherein the first correction function or the second correction function is a nonlinear function.

11. The method of claim 1, wherein the first correction function or the second correction function is dependent upon the primary measurement of the glucose analyte value.

12. The method of claim 1, wherein the first correction function or the second correction function is independent from the primary measurement of the glucose analyte value.

13. The method of claim 1, wherein obtaining the secondary measurement of the secondary effect include obtaining a temperature measurement.

14. The method of claim 1, wherein obtaining the secondary measurement of the secondary effect includes obtaining a hemoglobin measurement.

15. The method of claim 1, wherein obtaining the secondary measurement of the secondary effect includes obtaining a concentration of hematocrit.

16. A method for measuring a glucose analyte value in a blood sample via a biosensor, the method comprising:
    applying a fluid sample to a sensor element on a sensor strip of an electrochemical biosensor and obtaining an electrical output signal representing a primary measurement of the glucose analyte value, the biosensor being coupled to a meter function;
    obtaining a secondary measurement of a secondary effect via a secondary sensor or the meter function;
    comparing said secondary measurement of the secondary effect with a threshold value stored in a memory via at least one processor with a meter input coupled to the meter function;
    selecting, by the at least one processor, a first correction function from a plurality of correction functions if the secondary measurement is less than the threshold value;
    selecting, by the at least one processor, a second correction function from the plurality of correction functions if the secondary measurement is greater than the threshold value;
    wherein the first correction function and the second correction function comprise stored data indicative of a correction amount as a function of the secondary measurement;
    wherein the first correction function and the second correction function differ only by coefficient values;

the first correction function and the second correction function each outputting a correction value, the first correction function being independent of the primary measurement, the second correction function including an input of the primary measurement;

applying the primary measurement to the first correction function or the second correction function via the at least one processor to provide a corrected analyte value; and causing for display the corrected analyte value on a display communicatively coupled to the at least one processor.

17. A glucose analyte measurement system comprising:

a biosensor having a test strip operable to receive a fluid sample;

a memory storing a plurality of correction functions and a secondary threshold value;

a meter function coupled to the biosensor;

at least one processor coupled to the meter function and the memory, the at least one processor operable to:
send a signal through an electrode on the biosensor in contact with the fluid sample, and obtain an output signal associated with a primary measurement of a glucose analyte value from the meter function;
determine a secondary measurement of a secondary effect from the meter function or a secondary sensor;
compare the secondary measurement of the secondary effect with the stored threshold value;
select a first correction function if the secondary measurement is greater than the threshold value;
select a second correction function if the secondary measurement is less than the threshold value;
wherein the first correction function and the second correction function comprise stored data indicative of a correction amount as a function of the secondary measurement;
wherein the first correction function and the second correction function differ only by coefficient values; and
input the primary measurement to either first or second correction function to provide a corrected analyte value; and a display coupled to the at least one processor to display the corrected analyte value.

* * * * *